United States Patent [19]

Wheeless, Jr.

[11] Patent Number: 4,899,134

[45] Date of Patent: Feb. 6, 1990

[54] NEWBORN ANTI-THEFT DEVICE

[76] Inventor: Clifford R. Wheeless, Jr., 1006 St. Georges Rd., Baltimore, Md. 21210

[21] Appl. No.: 228,111

[22] Filed: Aug. 4, 1988

[51] Int. Cl.⁴ .............................................. G03B 23/00
[52] U.S. Cl. ..................................... 340/573; 340/539; 340/551; 340/572; 606/120
[58] Field of Search ............... 340/539, 571, 572, 573, 340/551, 552, 561, 825.05, 825.36, 825.49; 128/346, 321, 323

[56] References Cited

U.S. PATENT DOCUMENTS 4,598,272  7/1986  Cox ................................. 340/573 X
4,686,516  8/1987  Humphrey ........................ 340/572
4,777,477  10/1988 Watson ............................ 340/573

Primary Examiner—Reinhard J. Eisenzopf
Assistant Examiner—Robert W. Mueller
Attorney, Agent, or Firm—Cushman, Darby & Cushman

[57] ABSTRACT

A detectable element inconspicuously disposed in an umbilical cord clamp used to clamp the umbilical cord a newborn child allows the detection of unauthorized movement of the newborn child and prevents the possible abduction of the newborn child.

7 Claims, 2 Drawing Sheets

U.S. Patent    Feb. 6, 1990    Sheet 1 of 2    4,899,134
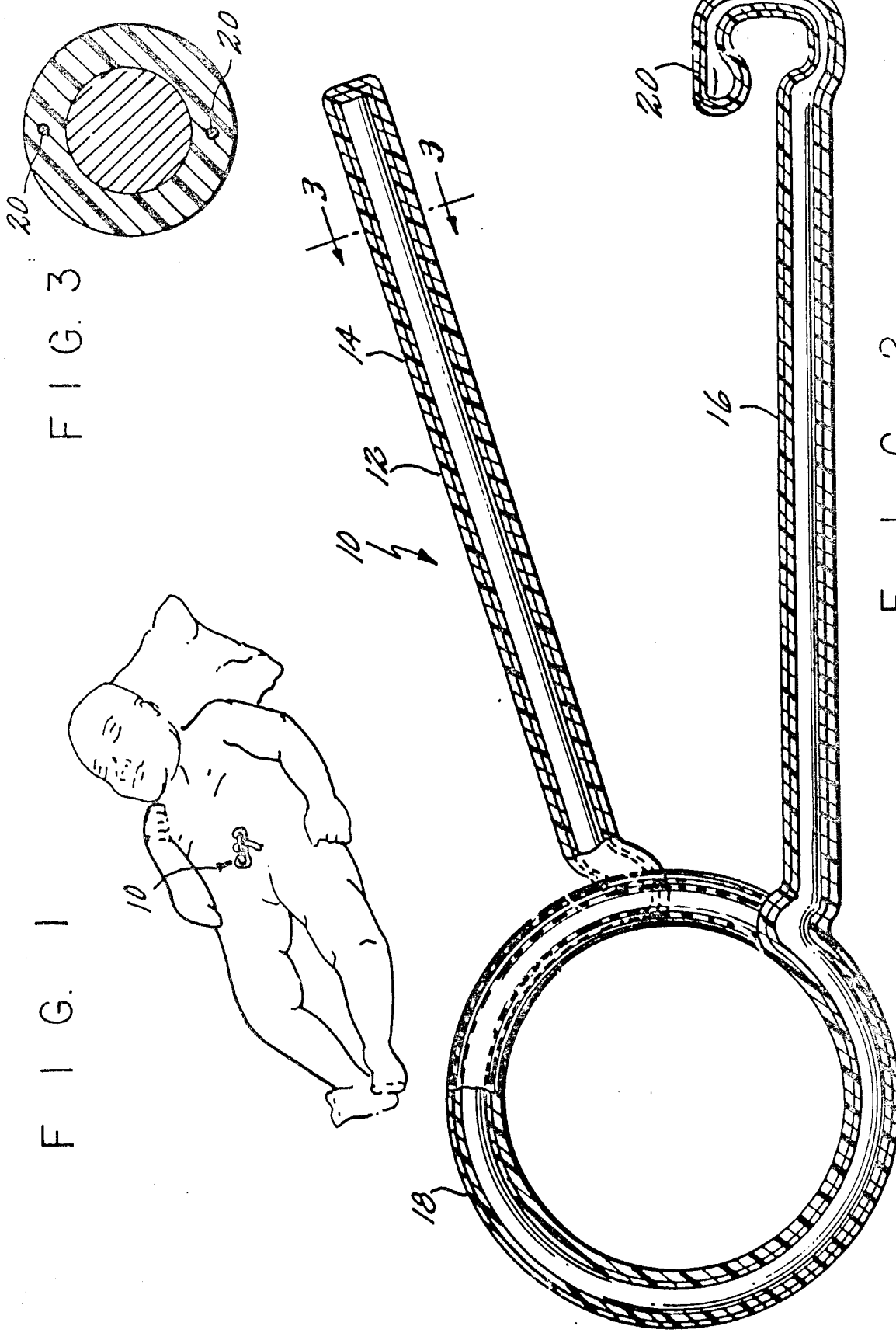

NEWBORN ANTI-THEFT DEVICE

BACKGROUND OF THE INVENTION

1. Field of the Art

The present invention relates to an anti-theft device that uses a detectable element disposed in an umbilical cord clamp.

2. Background of the Invention

In recent years, the abduction of newborn children from hospitals, has unfortunately become a problem. To reduce the chances of abduction, hospitals have increased security of newborns by having larger staffs watch over the newborn children and restricting access to maternity wards where these newborn children are kept.

However, these measures cannot adequately guard each newborn child. Once an abductor finds out where the maternity ward is located, it is very easy to wait until the ward area is empty, pick up a newborn child, and abscond with the child. Unless someone sees the absconder removing the newborn child, the abduction will probably be successful.

Therefore, an anti-theft device which can be used to prevent the abduction of newborn children is necessary. However, known monitoring devices cannot be effectively used.

U.S. Pat. No. 4,095,214 to Minasy discloses a responder device that can be attached using a strap to the ankle to monitor the movements of the person. However, the attachment of such a device to a newborn child is difficult. More importantly, even if this type of device were attached to an infant, it is easily recognizable as a security device. It would, therefore be very easy for an abductor to take the responder device off the newborn child and carry the newborn away without being detected.

Similarly, U.S. Pat. No. 4,471,345 to Barret discloses an identification tag that can be detected by various detection devices to determine the location of each of these tags. If this device were attached to a newborn child, it would also be easily recognizable as a type of security device, removed from the newborn child, and the abductor of the newborn child could then continue without detection.

Detection devices enclosed in special casings that can be attached to clothing or other merchandise that is sold in retail stores are well known. These devices could only be attached to the clothing of a newborn child and would be easily recognized as a detection device if so attached. These detection devices would be removed and will therefore not adequately allow detection of an attempted abduction.

The present inventor has therefore determined that an inconspicuous anti-theft device for monitoring the movement of newborn children while still in the hospital is needed, and has developed the following invention to satisfy this need.

SUMMARY OF THE INVENTION

The present invention provides an anti-theft device that can be attached to an infant and not be recognized as an anti-theft device. Because it is not recognizable as a anti-theft device, an abductor will not attempt to remove it from the newborn child. An appropriately placed detector will then detect the movement of the newborn child caused by the potential abduction. When an attempted abduction takes place, an alarm can then be given and the abductor apprehended.

The anti-theft device of the present invention is not recognized as an anti-theft device because it uses a detectable element disposed inconspicuously in an umbilical cord clamp. An umbilical cord clamp is placed on the umbilical cord stump of a newborn child to help ensure rapid closure of the umbilical cord without hemmorage or infection. Because all newborn children have this clamp placed upon their umbilical cord, an abductor will not think that it has any purpose other than a medical function.

Furthermore, different detectable elements can be used. In one embodiment, the detectable element is a wire loop coil that runs through the umbilical cord clamp.

In a second embodiment, the detectable element is a marker made of a material having a high permeability and a low coercivity that is placed within the umbilical cord clamp.

In both of these embodiments, a sensing system detects the presence of the detectable be element in a predetermined area. An AC magnetic field is established by a transmitting loop, for example, a large loop that is disposed within the doorway of an entrance. The presence of the detectable element is detected by a receiving loop when the transmitting loop and the detectable element are magnetically coupled. If the presence of the detectable element is detected, this indicates that the newborn child is also passing through this area. Detection of the detectable element as it passes a receiving loop can then indicate a possible abduction.

In a third embodiment of the present invention, a miniature radio transmitter is disposed in the umbilical cord clamp. The radio transmitter has the ability to transmit a signal that can be detected by receiver units that are used as the sensing system when the radio transmitter enters the predetermined area in which one of the receiver units is located. The receiver units can be placed, for instance, at a doorway exit. The transmitted radio signal can then be used to recognize the movement of a newborn child and avoid a possible abduction. It is also possible for radio transmitters installed in various anti theft devices to emit a coded signal so that the movement of the specific infant to which that particular device is attached can be monitored.

In all of these embodiments, an inconspicuous detectable element provides a nonrecognizeable anti-theft device which can be placed on a newborn child to prevent the abduction of the newborn.

BRIEF DESCRIPTION OF THE DRAWINGS

These and other advantages of the present invention may be appreciated from studying the following detailed description of the preferred embodiment together with the drawings in which:

FIG. 1 shows the anti-theft device of the present invention attached to a newborn child;

FIG. 2 shows a top view of a first embodiment of the present invention;

FIG. 3 shows a cross-section taken along line 3—3 in FIG. 2;

DETAILED DESCRIPTION OF THE PREFERRED EMBODIMENT

Figure 4:
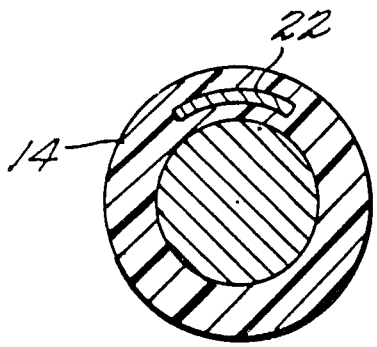
FIG. 4 shows a second embodiment of the present invention.

As shown in FIG. 1, a newborn child has attached at its umbilical cord an anti theft device 10 according to the present invention. As can be seen in FIG. 1, device 10 is inconspicuous because it only appears to serve a medical medical purpose, it also contains a detectable element that can be used to detect the movement of the newborn child.

As shown in FIG. 2, the umbilical cord clamp 12 includes clamping arms 14 and 16. Clamping arm 14 locks into the U-shaped end of clamping arm 16 so that the umbilical cord, which fits between clamping arms 14 and 16, stays closed. Tension producing portion 18 ensures that clamping arms 14 and 16 pressure the umbilical cord into a closed position. All types of umbilical cord clamps can be used with the present invention although only one type is disclosed in the drawings. Examples of umbilical cord clamps are found in U.S. Pat. Nos. 3,315,679 and 3,705,586, both to Sarracino. In this invention, as with all umbilical cord clamps, the whole device must be sterilized before initial use to prevent infection.

Examples of detectable elements are shown disposed in umbilical cord clamp 12 in more detail in the following embodiments. All U.S. patents referred to when describing these embodiments are incorporated by reference into this disclosure.

In the first embodiment, shown in FIGS. 2 and 3, the detectable element is made of a wire loop coil 20. In this embodiment, the umbilical cord clamp 12 is made of known plastic materials that acts as an umbilical cord clamp. The wire coil 20 is disposed inconspicuously inside the plastic and around the perimeter that makes up the umbilical cord clamp 12.

Wire loop coil 20 can be made of conductive material, such as high grade aluminum, that has a predetermined shape, diameter, and size. Multiple wire loop coils 20 can also be disposed within the umbilical cord clamp 12. Coils 20 can be detected in different spatial arrangements in accordance with the teachings of U.S. Pat. Nos. 4,628,324, and 4,549,186 to Grass.

An AC magnetic field emitted from a transmitting loop will cause an AC magnetic field having various harmonic components. The resulting AC magnetic field having different harmonic components can be sensed by a receiving loop. The received signal is then filtered by a filter circuit so that the presence of a desired harmonic component will trigger an alarm attached to the output of the filter circuit.

Both the transmitting loop and receiving loop can be, for example, large loops disposed in the doorway of the maternity ward or other exit area. The configuration of the transmitting loop and receiving loop can also be varied to improve the detection of the wire loop coil 20 as known in the art, and set forth, for example, in U.S. Pat. No. RE 32,667 to Humble and U.S. Pat. No. 4,309,697 to Weaver.

Filter circuits and alarm known in the art can be used to complete this sensing system.

FIG. 4 shows a second embodiment of the invention in which the detectable element is a metallic strip 22 that produces known harmonic frequencies that can be sensed by a sensing system comprised of a transmitting loop, a receiving loop, filter circuitry and an alarm as previously described. Metallic strip 22 is disposed in clamping arm 14. Metallic strip 22 is preferably a metallic material having high permeability and low coercitivity such as Permalloy. Various dimensions of metallic strip 22 can be used. U.S. Pat. No. 4,660,025 to Humphrey describes many different combinations of metallic materials and dimensions that could be employed.

Figure 5:
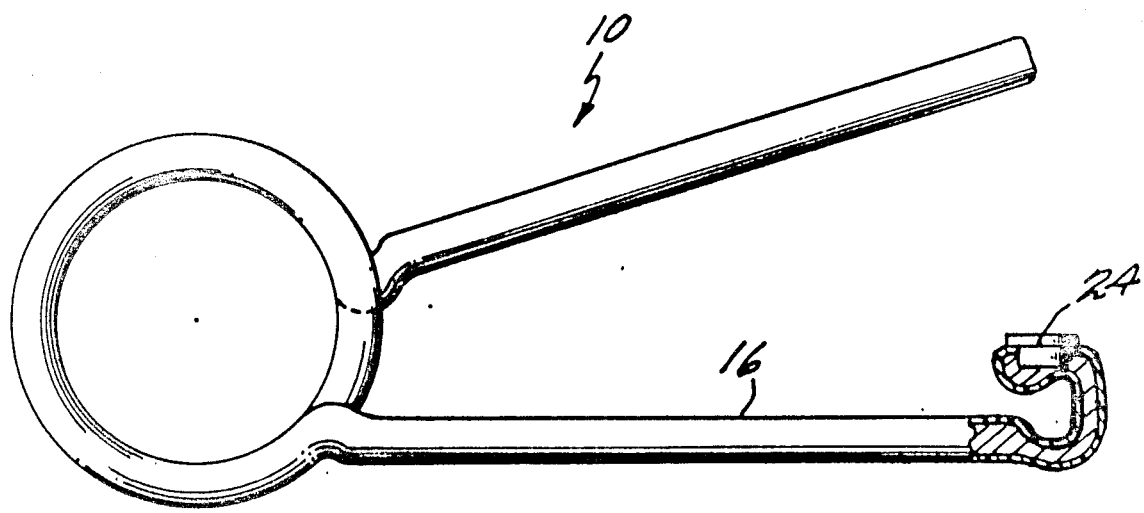
FIG. 5 shows a third embodiment of the present invention.

FIG. 5 shows a third embodiment of the present invention. In this embodiment, a miniature radio transmitter 24 disposed within the U-shaped portion of clamp arm 16 of umbilical cord clamp 12 makes up the anti-theft device of the present invention. Antenna 26, which emits the radio signal and is part of the radio transmitter 24, can be placed in the clamp arm 16. Depending on the type of umbilical cord clamp 12 being used, the placement of the radio transmitter 24, including antenna 26, can be varied as necessary.

In this embodiment, the radio transmitter produces a radio signal that is detected by a sensing system using receiver units arranged, for instance, at the exit of a maternity ward or other exit area, similar to the placement of the transmitting and receiving loops of the sensing system of the previous embodiments. The same radio signal can be used for all miniature radio transmitters 24 in use at one time or different coded radio signals can be used so that the movement of a specific infant can be detected.

Miniature radio transmitter 24 can, for instance, emit a radio signal in the microwave frequency range and be demodulated by an appropriate receiver to detect movement of a newborn child. Miniature radio transmitters as known in the art can be used to form the miniature radio transmitter 24.

Although this embodiment requires that the detectable element be an active device requiring power, rather than a passive element as in the previous embodiments, the short lifespan each anti-theft device would require only a small battery. This embodiment has the advantage of being able to emit a signal that can be easily detected no matter what the orientation of the anti-theft device 10 when it is in the predetermined area.

While the present invention has been described in connection with what is presently considered to be the most practical and preferred embodiments, it is to be understood that the invention is not limited to the disclosed embodiment, but is intended to cover various modifications and equivalent arrangements included within the spirit and scope of the following claims.

What is claimed is:

1. An apparatus for detecting the movement of a newborn within a predetermined area using a sensing system that causes an alarm comprising:
    an umbilical cord clamp; and
    detectable means disposed inconspicuously inside said umbilical cord clamp for triggering said sensing system and causing said alarm when said detectable means enters said predetermined area.

2. An apparatus according to claim 1 wherein said detectable means comprises a wire coil loop.

3. An apparatus according to claim 2 wherein said wire coil loop is disposed around the perimeter of said umbilical cord clamp.

4. An apparatus according to claim 1 wherein said detectable means is a metallic marker having a high permeability and a low coercitivity.

5. An apparatus according to claim 4 wherein said metallic marker is made of Permalloy.

6. An apparatus according to claim 1 wherein said detectable element is a radio transmitter.

7. An apparatus according to claim 6 wherein said radio transmitter is disposed at an end of a clamp arm of said umbilical cord clamp.

* * * * *